United States Patent
Cao

(10) Patent No.: US 8,551,720 B2
(45) Date of Patent: Oct. 8, 2013

(54) METHODS FOR DIAGNOSING BOWEL DISEASE

(75) Inventor: Deliang Cao, Chatham, IL (US)

(73) Assignee: The Board of Trustees of Southern Illinois University, Springfield, IL (US)

(*) Notice: Subject to any disclaimer, the term of this patent is extended or adjusted under 35 U.S.C. 154(b) by 248 days.

(21) Appl. No.: 12/739,371

(22) PCT Filed: Oct. 24, 2008

(86) PCT No.: PCT/US2008/081087
§ 371 (c)(1),
(2), (4) Date: Apr. 22, 2010

(87) PCT Pub. No.: WO2009/148470
PCT Pub. Date: Dec. 10, 2009

(65) Prior Publication Data
US 2010/0256009 A1    Oct. 7, 2010

Related U.S. Application Data

(60) Provisional application No. 61/000,440, filed on Oct. 25, 2007.

(51) Int. Cl.
*G01N 33/574*    (2006.01)

(52) U.S. Cl.
USPC .......................................................... 435/7.23

(58) Field of Classification Search
None
See application file for complete search history.

(56) References Cited

U.S. PATENT DOCUMENTS

2009/0186034 A1*    7/2009    Abbas et al. ............... 424/141.1

FOREIGN PATENT DOCUMENTS

WO    WO 2007/068985    *    6/2007

OTHER PUBLICATIONS

Kim et al (Annals of Clinical & Laboratory Science, 2003, 33:32-38).*

* cited by examiner

*Primary Examiner* — Laura B Goddard
(74) *Attorney, Agent, or Firm* — Polsinelli PC

(57) ABSTRACT

Provided herein are methods and materials for diagnosing a bowel disease in a subject by detecting the presence or absence of a bowel disease marker. A bowel disease marker has been identified as AKR1B10 and may be useful in identifying subjects at risk for bowel disease, predicting bowel disease progression, and assessing a subject's response to therapy.

18 Claims, 9 Drawing Sheets

AKR1B10, 10 × Objective

AKR1B10, 40 × Objective

Ki-67, 10 × Objective

Ki-67, 40 × Objective

A) AKR1B10 mRNA in colorectal cancer tissues

B) AKR1B10 protein in colorectal cancer tissues

A) AKR1B10 negative

B) AKR1B10 weakly positive

C) AKR1B10 positive

5 × Objective    40 × Objective

A) Disease-associated survival

B) Follow-up time of disease-free alive patients

A) AKR1B10 protein in colon diseases

B) Acrolein adducts in colon diseases

A). AKR1B10 knockdown

B). Acrolein-protein adducts

C). Immunocytochemistry (acrolein adducts)

Scrambled siRNA

AKR1B10 siRNA

A) AKR1B10 protein in gastrointestinal

B) AKR1B10 protein in gastrointestinal diseases

A) AKR1B10 mRNA in gastric cancer

B) AKR1B10 mRNA in small bowel cancer

C) AKR1B10 mRNA in colorectal cancer

METHODS FOR DIAGNOSING BOWEL DISEASE

CROSS-RELATED APPLICATIONS

This is the national stage of International Patent Application No. PCT/US2008/081087, filed on Oct. 24, 2008, which claims the benefit of U.S. Provisional Application No. 61/000,440, filed on Oct. 25, 2007, the contents of which are incorporated herein by reference.

FEDERALLY SPONSORED RESEARCH

This invention was made with government support under NIH Grant No. CA122622—National Cancer Institute. The government has certain rights in the invention.

FIELD OF THE INVENTION

The present invention relates to aldo-keto reductase family 1 B10 (AKR1B10) and its association with bowel diseases.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND

Gastrointestinal diseases, including inflammation and malignance, affect millions of people. For example, chronic ulcerative colitis and Crohn's disease affect roughly two million Americans and are often associated with the development of colorectal cancer. While there are more than 106,680 new cases of colorectal cancer diagnosed annually, accounting for more than 55,000 deaths each year in the U.S., the etiological factors and pathogenic mechanisms of these bowel diseases still remain, for the most part, unclear.

Electrophilic dietary carbonyls may be important pathogens of bowel diseases, including neoplasms. Food consumption often results in repeated exposure to various reactive carbonyls. Long term and cumulative carbonyl exposure may eventually result in carcinogenic changes to gastrointestinal cells. Therefore, early assessment of bowel disease severity may present the best opportunity for treatment intervention.

With the development of protein marker detection methods and genetic testing, it is possible to identify protein and nucleic acid markers that will be indicative of a propensity to develop disease or indicative of a disease state. There remains a need to identify one or more markers that are associated with bowel disease in a patient. These markers may represent a protein, a nucleic acid, and/or allelic variants, which may be useful in diagnosing bowel disease severity, and whose products may be targeted for early intervention therapy.

SUMMARY OF THE INVENTION

Provided herein is a method for determining a subject's predisposition for a bowel disease. The method may comprise providing a sample from a subject. A determination may be made as to whether the sample comprises a bowel disease ("BD") marker. The amount of a BD-marker in the subject sample may be measured and compared to an amount of the BD-marker as measured in a control sample. The subject's predisposition for bowel disease may increase as the difference in the amount of the BD-marker in the subject sample and the amount of the BD-marker in the control sample increases. The control sample may be from a subject that does not have a bowel disease. The control sample may comprise protein and/or nucleic acid. The sample from the subject may comprise protein and/or nucleic acid. An alternative method for determining a subject's predisposition for bowel disease may comprise providing a sample from a subject; and measuring for a BD-marker in the subject sample, wherein the subject is predisposed to bowel disease if the BD-marker is not present in the subject sample.

The protein from the control and/or subject sample may comprise a BD marker. The protein BD marker may be an AKR1B10 protein. The amino acid sequence of the AKR1B10 protein may be as shown in Table 1 (SEQ ID NO:2). The amount of AKR1B10 protein in the subject sample may be lower than the amount of AKR1B10 protein in the control sample. The protein BD-marker may be an acrolein-protein adduct. The acrolein-protein adduct may be carbonyl acrolein and cellular protein. The amount of acrolein-protein adduct in the subject sample may be higher than the amount of acrolein-protein adduct in the control sample.

The nucleic acid from the control and/or subject sample may comprise a BD-marker. The nucleic acid BD-marker may be a DNA, an mRNA, a SNP, and/or a mutation. The DNA or mRNA may encode AKR1B10. The DNA sequence encoding AKR1B10 may be SEQ ID NO:1. The AKR1B10-encoding mRNA in a subject sample may be in an amount that is lower than the amount of AKR1B10-encoding mRNA in the control sample. There may be no AKR1B10-encoding mRNA in a subject sample.

The bowel disease may be a colorectal disease, stomach disease, rectal disease, and/or a disease of the small intestine. The colorectal disease, stomach disease, rectal disease, and/or disease of the small intestine may be chronic colorectal disease, chronic inflammatory bowel disease, a malignant bowel disease, a cancer, neoplasia, dysplasia, adenoma, gastritis, inflammatory bowel disease, ulcerative colitis, and/or Crohn's disease. The cancer may be a colorectal cancer, stomach cancer, cancer of the small intestine, and/or cancer of the rectum.

Also provided herein is a method of detecting a bowel disease in a subject. The method may comprise providing a sample from a subject. A determination may be made as to whether the sample comprises a bowel disease ("BD") marker. The amount of a BD-marker in the subject sample may be measured and compared to an amount of the BD-marker as measured in a control sample. The subject's predisposition for bowel disease may increase as the difference in the amount of the BD-marker in the subject sample and the amount of the BD-marker in the control sample increases. The control sample may be from a subject that does not have a bowel disease. The control sample may comprise protein and/or nucleic acid. The sample from the subject may comprise protein and/or nucleic acid.

The protein from the control and/or subject sample may comprise a BD marker. The protein BD marker may be an AKR1B10 protein. The amino acid sequence of the AKR1B10 protein may be SEQ ID NO:2. The amount of AKR1B10 protein in the subject sample may be lower than the amount of AKR1B10 in the control sample. The protein BD-marker may be an acrolein-protein adduct. The amount of acrolein-protein adduct in the subject sample may be higher than the amount of acrolein-protein adduct in the control sample.

The nucleic acid from the control and/or subject sample may comprise a BD-marker. The nucleic acid BD-marker may be a DNA, an mRNA, a SNP, and/or a mutation. The DNA or mRNA may encode AKR1B10. The DNA sequence encoding AKR1B10 may be SEQ ID NO:1. The AKR1B10-encoding mRNA may be in an amount that is lower than the amount of AKR1B10-encoding mRNA in the control sample. There may be no AKR1B10-encoding mRNA in a subject sample.

The bowel disease may be a colorectal disease, stomach disease, rectal disease, and/or a disease of the small intestine. The colorectal disease, stomach disease, rectal disease, and/or disease of the small intestine may be chronic colorectal disease, chronic inflammatory bowel disease, a malignant bowel disease, a cancer, neoplasia, dysplasia, adenoma, gastritis, inflammatory bowel disease, ulcerative colitis, and/or Crohn's disease. The cancer may be a colorectal cancer, stomach cancer, cancer of the small intestine, and/or cancer of the rectum.

In any of the foregoing methods, the BD-marker may be a mutation or a single nucleotide polymorphism ("SNP"). The mutation or SNP may be detected by amplifying a nucleic acid comprising the marker and detecting the amplified nucleic acids, thereby detecting the marker. The marker may be detected by sequencing. An mRNA marker may be detected by reverse transcription PCR (rtPCR). The rtPCR may be real time rtPCR Also provided herein is a method of treating a subject identified as having a predisposition to a bowel disease or a subject identified as having a bowel disease. The method may comprise administering an anti-infection agent to the subject. The anti-infection agent may be an anti-inflammatory, antibiotic, immunosuppressant, chemotherapeutic, anti-diarrheal, and/or fluid replacement agent. The anti-inflammatory agent may be an IL-1 blocker, sulfasalazine, mesalamine, and/or a corticosteroid. The IL-1 blocker may be rilonacept, anakinra, and/or Zn-protoporphyrin (ZnPP). The antibacterial agent may be an antibiotic such as an aminoglycoside, amoxicillin, levofloxacin, dicloxacillin, cephalexin, amoxicillin/clavulanate, erythromycin, clarithromycin, azithromycin, clindamycin, cefuroxime axetil, cefprozil, cefixime, cefpodoxime proxetil, loracarbef, ciprofloxacin, tobramycin, colistin, trimethoprim/sulfamethoxazole, doxycycline, minocycline, cefazolin, nafcillin, vancomycin, β-lactam, ceftazidime, ticarcillin, piperacillin, imipenem, meropenem, aztreonam, an aminoglycoside, amikacin, merpenem, ceftazidime, chloramphenicol, ticarcillin/clavulanate, aztreonam, imipenem, a polypeptide antibiotic, and/or meropenem. The polypeptide antibiotic may be of the polymyxin class of antibiotics. A broad range antibiotic may be used in the regimen. A broad range antibiotic may include levofloxacin or amoxycillin. An immune system suppressor may be any immune suppressing agent. The immune suppressing agent may be azathioprine or mercaptopurine. An anti-diarrheal may be diphenoxylate, loperamide, and/or codeine. Subjects who are dehydrated may be treated with a fluid and/or an electrolyte. The method of treating a subject identified as having a predisposition to a bowel disease or a subject identified as having a bowel disease may comprise administering an agent that activates or reactivates expression or function of a BD marker. The method of treating a subject identified as having a predisposition to a bowel disease or a subject identified as having a bowel disease may comprise administering an agent that inhibits or represses expression or function of a BD marker.

Also provided herein is a method of preventing bowel disease in a subject. The method may comprise determining whether a subject has a predisposition for a bowel disease. If the subject has a predisposition for a bowel disease, administering an agent that activates or reactivates AKR1B10 gene expression and/or protein function in the subject.

The method of treating a subject identified as having a predisposition to a bowel disease or a subject identified as having a bowel disease may comprise administering an agent that activates, or reactivates, expression and/or function of an AKR1B10 gene or protein.

Also provided herein is a method for monitoring the progression of bowel disease in a subject. The method may comprise providing a sample from a subject. A determination may be made as to whether the sample comprises a bowel disease ("BD") marker. The amount of a BD-marker in the subject sample may be measured and compared to an amount of the BD-marker as measured in a control sample. The method may comprise comparing the amount of the BD-marker in the subject sample, obtained prior to administration of a bowel disease treatment, to the amount in a second subject sample, obtained after administration of a bowel disease treatment. The method may comprise comparing the amount of the BD-marker in the subject sample to the amount of BD-marker in a control sample, wherein the control sample is taken from the subject being monitored and is taken at a time prior to when the subject sample is taken. The control sample may be taken minutes, hours, days, weeks, months, or years prior to the subject sample being taken. One may determine progression of a bowel disease based upon a difference in the amount of the BD-marker in the subject sample and the amount of the BD-marker in the control sample, and/or second subject sample. The control sample may be from a subject that does not have a bowel disease. The control sample may comprise protein and/or nucleic acid. The sample from the subject may comprise protein and/or nucleic acid. The level, or extent, of monitoring may be predicated on a subject's predisposition to bowel disease. A high-risk subject may require a higher level of, or more stringent, monitoring.

The protein from the control and/or subject sample may comprise a BD marker. The protein BD-marker may be AKR1B10 protein. The amino acid sequence of the AKR1B10 protein may be SEQ ID NO:2. The protein BD-marker may be an acrolein-protein adduct.

The nucleic acid from the control and/or subject sample may comprise a BD-marker. The nucleic acid BD-marker may be a DNA, an mRNA, a SNP, and/or a mutation. The DNA or mRNA may encode AKR1B10. The DNA or mRNA may encode an acrolein-protein adduct.

The bowel disease may be a colorectal disease, stomach disease, rectal disease, and/or a disease of the small intestine. The colorectal disease, stomach disease, rectal disease, and/or disease of the small intestine may be chronic colorectal disease, chronic inflammatory bowel disease, a malignant bowel disease, a cancer, neoplasia, dysplasia, adenoma, gastritis, inflammatory bowel disease, ulcerative colitis, and/or Crohn's disease. The cancer may be a colorectal cancer, stomach cancer, cancer of the small intestine, and/or cancer of the rectum.

Also provided herein is a kit for performing a method for diagnosing severity of bowel disease in a subject, for identifying a subject's predisposition for bowel disease, and/or for performing a population survey to identify person at high risk for bowel disease. The kit may comprise a means for collecting a DNA or protein sample, a means for detecting a BD-marker, a control sample, and instructions for performing the method of diagnosis. The control sample may comprise nucleic acid and/or protein from a subject that does not have a bowel disease. The kit may comprise one or more oligonucleotides, probes, and/or primers. The oligonucleotides, siRNA, probes, and/or primers may be commercially available. The siRNA may be SEQ ID NO:1 and/or SEQ ID NO:2.

DETAILED DESCRIPTION

Figure 1:
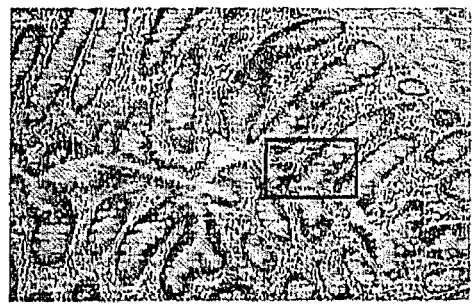
FIG. 1 shows adjacent paraffin sections from a trauma patient. The sections were stained with AKR1B10 and Ki-67 antibodies. Ki-67 staining indicates the dividing cells.
Figure 1:
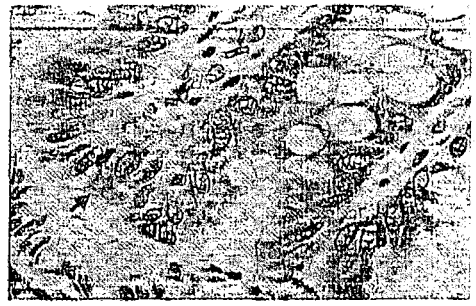
Figure 1:
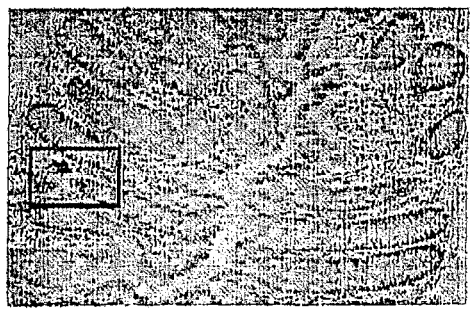
Figure 1:
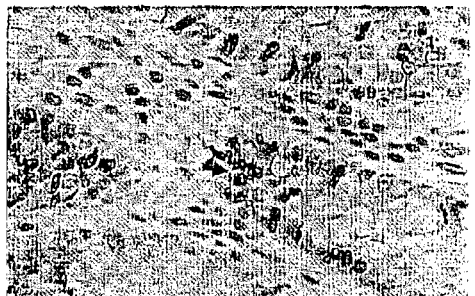

The inventors have made the surprising discovery that there is an association between bowel disease and certain protein and genetic markers. These markers, or bowel disease ("BD")-markers, may be in one or more aldo-keto reductase genes and/or in one or more regulators of aldo-keto reductase expression and/or function. The identification of a BD-marker in a subject may be useful in predicting bowel disease progression and assessing the subject's response to therapy and/or identifying a sub-population of people who are at risk of a bowel disease. In addition, knowledge of a particular marker associated with susceptibility to developing an inflammation or a neoplastic disease may allow one to customize the prevention or treatment in accordance with the subject's genetic profile. Early detection of a BD-marker, or realization of a lack thereof, may allow the subject to delay or prevent bowel disease, or to have more stringent monitoring of a bowel disease, such as chronic gastritis, chronic inflammatory bowel disease and/or malignant bowel disease. A subject who has, or does not have, a BD-marker may be treated with an agent that activates BD marker expression or function, an agent that reactivates BD marker expression or function, chemotherapy, an antibiotic and/or an anti-inflammatory regimen.

The ability to target populations expected to show the highest clinical benefit, based on genetic or protein profile, may enable the repositioning of already marketed drugs, the rescue of drug candidates whose clinical development has been discontinued as a result of safety or efficacy limitations, which may be patient sub-group-specific, and/or an accelerated and less costly development of candidate therapeutics.

The methods and materials described below use genetic and protein analyses to determine the level of, absence of, or presence of a BD-marker and reveal whether a subject may have a bowel disease or whether a subject may be predisposed to a bowel disease.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

a. Bowel

"Bowel" as used herein may mean a stomach, small and large intestine, a rectum, an alimentary canal extending from the stomach to the anus, a gall bladder, and/or bile duct. In humans and other mammals, the alimentary canal may consist of four segments, the stomach, the small intestine, the large intestine, and the rectum.

b. Fragment

"Fragment" as used herein may mean a portion of a reference peptide or polypeptide or nucleic acid sequence.

c. Identical

"Identical" or "identity" as used herein in the context of two or more polypeptide or nucleotide sequences, may mean that the sequences have a specified percentage of residues or nucleotides that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

d. Label

"Label" or "detectable label" as used herein may mean a moiety capable of generating a signal that allows the direct or indirect quantitative or relative measurement of a molecule to which it is attached. The label may be a solid such as a microtiter plate, particle, microparticle, or microscope slide; an enzyme; an enzyme substrate; an enzyme inhibitor; coenzyme; enzyme precursor; apoenzyme; fluorescent substance; pigment; chemiluminescent compound; luminescent substance; coloring substance; magnetic substance; or a metal particle such as gold colloid; a radioactive substance such as $^{125}I$, $^{131}I$, $^{32}P$, $^{3}H$, $^{35}S$, or $^{14}C$; a phosphorylated phenol derivative such as a nitrophenyl phosphate, luciferin derivative, or dioxetane derivative; or the like. The enzyme may be a dehydrogenase; an oxidoreductase such as a reductase or oxidase; a transferase that catalyzes the transfer of functional groups, such as an amino; carboxyl, methyl, acyl, or phosphate group; a hydrolase that may hydrolyzes a bond such as ester, glycoside, ether, or peptide bond; a lyases; an isomerase; or a ligase. The enzyme may also be conjugated to another enzyme.

The enzyme may be detected by enzymatic cycling. For example, when the detectable label is an alkaline phosphatase, a measurement may be made by observing the fluorescence or luminescence generated from a suitable substrate, such as an umbelliferone derivative. The umbelliferone derivative may comprise 4-methyl-umbellipheryl phosphate.

The fluorescent or chemiluminescent label may be a fluorescein isothiocyanate; a rhodamine derivative such as rhodamine B isothiocyanate or tetramethyl rhodamine isothiocyanate; a dancyl chloride (5-(dimethylamino)-1-naphtalenesulfonyl chloride); a dancyl fluoride; a fluorescamine (4-phenylspiro[furan-2(3H); 1ÿ-(3ÿH)-isobenzofuran]-3;3ÿ-dione); a phycobiliprotein such as a phycocyanine or physoerythrin; an acridinium salt; a luminol compound such as lumiferin, luciferase, or aequorin; imidazoles; an oxalic acid ester; a chelate compound of rare earth elements such as europium (Eu), terbium (Tb) or samarium (Sm); or a coumarin derivative such as 7-amino-4-methylcoumarin.

The label may also be a hapten, such as adamantine, fluoroscein isothiocyanate, or carbazole. The hapten may allow the formation of an aggregate when contacted with a multi-valent antibody or (strep)avidin containing moiety. The hapten may also allow easy attachment of a molecule to which it is attached to a solid substrate.

The label may be detected by quantifying the level of a molecule attached to a detectable label, such as by use of electrodes; spectrophotometric measurement of color, light, or absorbance; or visual inspection.

e. Substantially Identical

"Substantially identical," as used herein may mean that a first and second protein or nucleotide sequence are at least 50%-99% identical over a region of 8-100 or more amino acids nucleotides.

2. Methods of Diagnosis and Monitoring

Provided herein is a method of determining a subject's predisposition for a bowel disease. The method may measure a biomarker level in a subject sample and compare the level to the biomarker level in a control sample. The subject may be predisposed to bowel disease if the biomarker in the subject sample is absent, or if the level of the biomarker in the subject sample is lower or higher than the level of the biomarker in the control sample. The subject's predisposition may increase as the difference between the amount of the biomarker in the subject sample and the amount of the biomarker in the control sample increases. An alternative method for determining a subject's predisposition for bowel disease may comprise providing a sample from a subject; and measuring for a BD-marker in the subject sample, wherein the subject is predisposed to bowel disease if the BD-marker is not present in the subject sample. The method of determining a subject's predisposition for a bowel disease may be part of a population survey to identify those persons at risk for, or have, a bowel disease.

Also provided herein is a method of detecting bowel disease in a subject. The method may comprise measuring a biomarker expression level in a subject sample and comparing the level to the biomarker expression level in a control sample. The subject may have a bowel disease if the biomarker is not present in the subject sample, or if the amount of the biomarker in the subject sample is lower or higher than the amount of the biomarker in the control sample.

Also provided herein is a method of monitoring a subject for bowel disease. The subject may have been determined to have a predisposition for bowel disease. The subject may already have a bowel disease. It may be desirable to measure the effects of treatment on the bowel disease by treating the patient using a method comprising monitoring the bowel disease. Monitoring for bowel disease may include measuring for the presence, absence, or level of a protein marker or nucleic acid marker in a subject sample, measuring the for the presence, absence, or level of the protein marker or nucleic acid in a control sample, and determining the progression of the bowel disease when there is a difference between the amount of the protein or nucleic acid marker in the subject sample and the protein or nucleic acid marker in the control sample. The control sample may be sample from the subject that was taken prior to administration of a treatment. The control sample may be from a normal, healthy subject or from a subject that does not have a bowel disease.

Also provided herein is a method of identifying a subject as having a high risk for a bowel disease. The method may be part of a population survey to identify those subjects having a high risk for a bowel disease. The method may measure a biomarker level in a subject sample and compare the level to the biomarker level in a control sample. The subject may be at high risk for bowel disease if the biomarker in the subject sample is absent, or if the level of the biomarker in the subject sample is lower or higher than the level of the biomarker in the control sample. The subject's risk for bowel disease may increase as the difference between the amount of the biomarker in the subject sample and the amount of the biomarker in the control sample increases. An alternative method for determining a subject's risk for bowel disease may comprise providing a sample from a subject; and measuring for a BD-marker in the subject sample, wherein the subject is at high risk for bowel disease if the BD-marker is not present in the subject sample.

In any of the methods described herein, the biomarker in a subject sample may be at least 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 10.5-fold, 11-fold, 11.5-fold, 12-fold, 12.5-fold, 13-fold, 13.5-fold, 14-fold, 14.5-fold, 15-fold, 20-fold, 25-fold, 30-fold, 35-fold, 40-fold, 45-fold, 50-fold, 55-fold, 60-fold, 65-fold, or 70-fold less, or more, than the biomarker in the control sample.

In any of the methods described herein, the biomarker in a subject sample may be between 1% and 10%, between 11% and 20%, between 21% and 30%, between 31% and 40%, between 41% and 50%, between 51% and 60%, between 61% and 70%, or between 1% and 40% less, or more, than the biomarker in the control sample. In any of the methods described herein, the biomarker in a subject sample may be at least 5%, 10%, 15%, 20%, 25%, 30%, 40%, 45%, 50%, 55%, 60%, 65%, 70%, 75%, 80%, 85%, 90%, or 95% less, or more, than the biomarker in the control sample.

a. BD-Marker

The biomarker may be a bowel disease (BD) marker. The bowel disease marker may be a genetic marker. The detection of the presence or absence of a genetic marker, or the detection of a genetic marker level or quantity, or lack thereof, in a nucleic acid-containing sample from the subject may be indicative of a predisposition for a bowel disease. The genetic marker may be a nucleic acid. The nucleic acid may be DNA or RNA. The RNA may be mRNA. The nucleic acid may encode a protein that regulates the activity and/or expression of an aldo-keto reductase, such as C-fos and/or C-jun. C-fos and/or C-jun may upregulate AKR1B10 gene expression. The nucleic acid may encode an aldo-keto reductase gene (SEQ ID NO:1). The aldo-keto reductase gene may be aldo-keto reductase family 1 B10 (AKR1B10).

The genetic marker may be a mutation. The mutation may be a polymorphism, a deletion, a substitution, an insertion, and/or a frameshift mutation. The mutation may be in a gene that encodes a protein that regulates the activity and/or expression of an aldo-keto reductase. The mutation may be in an aldo-keto reductase gene. The aldo-keto reductase gene may be aldo-keto reductase family 1 B10 (AKR1B10). The polymorphism may be a single nucleotide polymorphism (SNP). The marker may be detected as a SNP or a fragment tase may be aldo-keto reductase family 1 B10 (AKRB10). The protein BD-marker may be a protein that regulates the activity and/or expression of an aldo-keto reductase. The protein marker may be an acrolein-protein adduct.

The determination of whether a subject is at high risk of a bowel disease, predisposed to a bowel disease, or the diagnosis of a subject having bowel disease, may be based upon the detection of the protein or genetic marker in combination with one or more other markers. The one or more other markers may be a protein or genetic marker. The one or more other protein or genetic markers may be carcinoembryonic antigen (CEA), acrolein-protein adduct, carbohydrate antigen (CA) 19-9, carbohydrate antigen (CA) 72-4, tissue polypeptide antigen (TPA), p53 mutation, K-ras mutation, and/or any other diagnosed chromosomal mutation, deletion, or translocation.

TABLE 1

| SEQUENCE | SEQ ID NO. |
|---|---|
| AKR1B10 DNA SEQUENCE:<br>caaaaacagc aacagaaagc aggacgtgag acttctacct gctcactcag aatcatttct<br>gcaccaacca tggccacgtt tgtggagctc agtaccaaag ccaagatgcc cattgtgggc<br>ctgggcactt ggaagtctcc tctcggcaaa gtgaaagaag cagtgaaggt ggccattgat<br>gcaggatatc ggcacattga ctgtgcctat gtctatcaga atgaacatga agtgggggaa<br>gccatccaag agaagatcca agagaaggct gtgaagcggg aggacctgtt catcgtcagc<br>aagttgtggc ccactttctt tgagagaccc cttgtgagga aagcctttga gaagacctc<br>aaggacctga agctgagcta tctgacgtc tatcttatc actggccaca gggattcaag<br>tctggggatg accttttccc caaagatgat aaaggtaatg ccatcggtgg aaaagcaacg<br>ttcttggatg cctgggaggc catggaggga ctggtggatg aggggctggt gaaagcctt<br>ggggtctcca atttcagcca cttccagatc gagaagctct tgaacaaacc tggactgaaa<br>tataaaccag tgactaacca ggttgagtgt cacccatacc tcacgcagga gaaactgatc<br>cagtactgcc actccaaggg catcaccgtt acggcctaca gcccctggg ctctccggat<br>agaccttggg ccaagccaga agacccttcc ctgctggagg atcccaagat taaggagatt<br>gctgcaaagc acaaaaaaac cgcagcccag gttctgatcc gtttccatat ccagaggaat<br>gtgattgtca tccccaagtc tgtgacacca gcacgcattg ttgagaacat tcaggtcttt<br>gactttaaat tgagtgatga ggagatggca accatactca gcttcaacag aaactggagg<br>gcctgtaacg tgttgcaatc ctctcatttg gaagactatc ccttcgatgc agaatattga<br>ggttgaatct cctggtgaga ttatacagga gattctcttt cttcgctgaa gtgtgactac<br>ctccactcat gtccattttt agccaagctt atttaagatc acagtgaact tagtcctgtt<br>atagacgaga atcgaggtgc tgttttagac atttatttct gtatgttcaa ctaggatcag<br>aatatcacag aaaagcatgg cttgaataag gaaatgacaa ttttttccac ttatctgatc<br>agaacaaatg tttattaagc atcagaaact ctgccaacac tgaggatgta aagatcaata<br>aaaaaaataa taatcat | SEQ ID NO: 1 |
| AKR1B10 AMINO ACID SEQUENCE:<br>MATFVELSTKAKMPIVGLGTWKSPLGKVKEAVKVAIDAGYRHIDCAYVYQN<br>EHEVGEAIQEKIQEKAVKREDLFIVSKLWPTFFERPLVRKAFEKTLKDLKLSYL<br>DVYLIHWPQGFKSGDDLFPKDDKGNAIGGKATFLDAWEAMEELVDEGLVKA<br>LGVSNFSHFQIEKLLNKPGLKYKPVTNQVECHPYLTQEKLIQYCHSKGITVTA<br>YSPLGSPDRPWAKPEDPSLLEDPKIKEIAAKHKKTAAQVLIRFHIQRNVIVIPKS<br>VTPARIVENIQVFDFKLSDEEMATILSFNRNWRACNVLQSSHLEDYPFDAEY | SEQ ID NO: 2 | thereof. The fragment may be between 10 and 500 nucleotides, between 50 and 400 nucleotides, between 100 and 300 nucleotides, between 200 and 250 nucleotides, between 10 and 50 nucleotides, between 10 and 20 nucleotides, between 10 and 30 nucleotides, or between 10 and 40 nucleotides in length.

Within a population, a mutation may be assigned a minor allele frequency. There may be variations between subject populations. A marker that is common in one geographical or ethnic group may be more rare in another. The marker may be overrepresented or underrepresented in a group of subjects. Subjects may be divided into groups on the basis of age, sex/gender, and/or race.

The BD-marker may be a protein marker. The detection of the presence or absence of a protein marker, or the detection of a protein marker level or quantity, or lack thereof, in a protein-containing sample from the subject may be indicative of a predisposition for a bowel disease. The protein BD-marker may be an aldo-keto reductase. The aldo-keto reducb. Bowel Disease The bowel disease may be a colorectal disease, stomach disease, rectal disease, and/or a disease of the small intestine. The colorectal disease, stomach disease, rectal disease, and/or disease of the small intestine may be chronic colorectal disease, chronic inflammatory bowel disease, a malignant bowel disease, a cancer, neoplasia, dysplasia, adenoma, gastritis, inflammatory bowel disease, ulcerative colitis, and/or Crohn's disease. The cancer may be a colorectal cancer, stomach cancer, cancer of the small intestine, and/or cancer of the rectum.

c. Subject

The subject may be a human. The human may be healthy. The human may not exhibit symptoms of an illness. The human may be ill. The illness may be constipation, thin stool, stomach cramps, hematochezia, unexplained weight loss, a consistent sense of fullness, nausea and/or vomiting, and/or lethargy. The human may be diagnosed with having a non- or pre-malignant growth or dysplasia. The non- or pre-malignant growth may be an adenomatous polyp. The illness, non- or pre-malignant growth, or dysplasia, may result from any mutation in a nucleotide sequence that results in an alteration in the expression level of a genetic marker or a protein marker. The resultant level or amount of the marker may be lower or higher than the level of the marker in a control. The resultant level may be non-existent as compared to the level of the marker in a control. The control may be a sample from a subject that does not have a bowel disease.

d. Sample

The sample may be a subject sample and/or a control sample. The sample may comprise nucleic acid and/or protein from a subject. The nucleic acid may be DNA or RNA. The nucleic acid may be genomic. The sample may be used directly as obtained from the subject or following pretreatment to modify a character of the sample. Pretreatment may include extraction, concentration, inactivation of interfering components, and/or the addition of reagents. The subject and control sample may be derived from the same organism but may also be derived from different organisms/individuals. The subject sample may comprise tissue cultures or cell cultures. The subject and/or control sample may comprise the same kind of cell(s) and/or tissue(s).

Any cell type, tissue, or bodily fluid may be utilized to obtain a sample. Such cell types, tissues, and fluid may include sections of tissues such as biopsy and autopsy samples, frozen sections taken for histologic purposes, blood, plasma, serum, sputum, stool, tears, mucus, saliva, hair, and skin. Cell types and tissues may also include gastrointestinal cells or fluid, inflammatory tissue, premalignant adenomas, colorectal cancer, lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an organism, but can also be accomplished by using previously isolated cells (e.g., isolated by another person, at another time, and/or for another purpose). Archival tissues, such as those having treatment or outcome history, may also be used. The tissue may be a gastric cancer tissue, a small intestine cancer tissue, and/or an inflamed tissue. The sample may be frozen, formalin-fixed, and/or paraffin-embedded. Nucleic acid purification may not be necessary.

e. Detection

The BD-marker may be detected in a sample derived from the patient. Many methods are available for detecting a marker in a subject and may be used in conjunction with the herein described methods. These methods may depend upon whether the BD-marker is a genetic or protein marker.

Genetic marker detection methods may include large-scale SNP genotyping, exonuclease-resistant nucleotide detection, solution-based methods, genetic bit analyses, primer guided nucleotide incorporation, reverse transcription PCR (rtPCR), real-time rtPCR, allele specific hybridization, transcription-based methods and analyses, reverse transcription methods and analyses, Northern blot methods, in situ hybridization, in vitro amplification, and other techniques. Any method of detecting a marker may use a labeled oligonucleotide.

Protein marker detection methods may include immunoassays, such as ELISA, immunohistochemistry, in situ immunohistochemistry, and radioimmunoassay, which utilize antibodies specific for the protein of interest; mass spectrometry; electrophysiological techniques to detect protein from specific cells; expression profiling; immunohistochemistry; western blot methods and analysis; microarray analysis; and immuno-polymerase chain reaction (immuno-PCR). Standard labeling methods may include fluorescence, radioisotopes, and enzymes such as peroxidase and phosphatase. In addition, secondary antibodies may be biotinylated to increase sensitivity. Any protein marker detection method may use an antibody that binds AKR1B10. Any protein marker detection method may use an antibody that binds an acrolein-protein adduct. The antibody may specifically bind to human AKR1B10. The antibody may specifically bind to a human acrolein-protein adduct. The antibody may comprise polyclonal antisera. The antibody may be a monoclonal antibody. The antibody may be one as disclosed in WO 2008/101184 (PCT/US2008/054124), which is incorporated herein by reference in its entirety.

(1) Large Scale SNP Genotyping

Large scale SNP genotyping may include any of dynamic allele-specific hybridization (DASH), microplate array diagonal gel electrophoresis (MADGE), pyrosequencing, oligonucleotide-specific ligation, or various DNA "chip" technologies such as Affymetrix SNP chips. These methods may require amplification of the target genetic region. Amplification may be accomplished via polymerase chain reaction (PCR).

(2) Exonuclease-Resistant Nucleotide

BD-markers may be detected using a specialized exonuclease-resistant nucleotide, as described in U.S. Pat. No. 4,656,127, which is incorporated herein by reference. A primer complementary to the allelic sequence immediately 3' to the polymorphic site may be permitted to hybridize to a target molecule obtained from the subject. If the polymorphic site on the target molecule contains a nucleotide that is complementary to the particular exonuclease-resistant nucleotide derivative present, then that derivative may be incorporated onto the end of the hybridized primer. Such incorporation may render the primer resistant to exonuclease, and thereby permit its detection. Since the identity of the exonuclease-resistant derivative of the sample may be known, a finding that the primer has become resistant to exonuclease reveals that the nucleotide present in the polymorphic site of the target molecule was complementary to that of the nucleotide derivative used in the reaction. This method may not require the determination of large amounts of extraneous sequence data.

(3) Solution-Based Method

A solution-based method may be used to determine the identity of a BD-marker, as described in PCT Application No. WO91/02087, which is herein incorporated by reference. A primer may be employed that is complementary to allelic sequences immediately 3' to a polymorphic site. The method may determine the identity of the nucleotide of that site using labeled dideoxynucleotide derivatives that, if complementary to the nucleotide of the polymorphic site, will become incorporated onto the terminus of the primer.

(4) Genetic Bit Analysis

Genetic bit analysis may use mixtures of labeled terminators and a primer that is complementary to the sequence 3' to a polymorphic site. A labeled terminator may be incorporated, wherein it is determined by and complementary to, the nucleotide present in the polymorphic site of the target molecule being evaluated. The primer or the target molecule may be immobilized to a solid phase.

(5) Primer-Guided Nucleotide Incorporation

A primer-guided nucleotide incorporation procedure may be used to assay for a BD-marker in a nucleic acid, as described in Nyren, P. et al., Anal. Biochem. 208:171-175 (1993), which is herein incorporated by reference. Such a procedure may rely on the incorporation of labeled deoxynucleotides to discriminate between bases at a polymorphic site. In such a format, since the signal is proportional to the number of deoxynucleotides incorporated, polymorphisms that occur in runs of the same nucleotide may result in signals that are proportional to the length of the run.

(6) Allele Specific Hybridization

Allele specific hybridization may be used to detect a BD-marker. This method may use a probe capable of hybridizing to a target allele. The probe may be labeled. A probe may be an oligonucleotide. The target allele may have between 3 and 50 nucleotides around the marker. The target allele may have between 5 and 50, between 10 and 40, between 15 and 40, or between 20 and 30 nucleotides around the marker. A probe may be attached to a solid phase support, e.g., a chip. Oligonucleotides may be bound to a solid support by a variety of processes, including lithography. A chip may comprise more than one allelic variant of a target region of a nucleic acid, e.g., allelic variants of two or more polymorphic regions of a gene.

(7) Real-Time RT-PCR

Real-time RT-PCR may be used to detect a BD-marker. By using reverse transcriptase to convert mRNA into complementary DNA (cDNA), which is then amplified by PCR and, again analyzed by agarose gel electrophoresis, one may quantitate mRNA level(s) in a sample. Real-time RT-PCR may quantitate reaction products for each sample in every PCR cycle. The result may be a broad $10^7$-fold dynamic range. Data analysis, including standard curve generation and copy number calculation, may be performed automatically.

Different chemistries may be used for real-time RT-PCR. Four different chemistries, TaqMan® (Applied Biosystems, Foster City, Calif., USA), Molecular Beacons, Scorpions® and SYBR® Green (Molecular Probes), are available for real-time PCR. Each of these chemistries allows detection of PCR products via the generation of a fluorescent signal.

(8) Western Blot and ELISA

Western blot and/or enzyme-linked immunosorbent assays (ELISA) may be used to detect a BD-marker. Both techniques are well known in the art. Western blotting may use gel electrophoresis to separate native or denatured proteins via the length of the polypeptide (denaturing conditions) or by the 3-D structure of the protein (native/non-denaturing conditions). The proteins may then be transferred to a membrane where they may be detected using antibodies specific to the target protein.

Other related techniques include using antibodies to detect proteins in tissues and cells by immunostaining and enzyme-linked immunosorbent assay (ELISA). The purpose of an ELISA is to determine if a particular protein is present in a sample and if so, how much.

(9) Other Genetic Marker Detection Techniques

Examples of other techniques for detecting alleles include selective oligonucleotide hybridization, selective amplification, or selective primer extension. Oligonucleotide primers may be prepared in which the known mutation or nucleotide difference is placed centrally and then hybridized to target DNA under conditions which permit hybridization if a perfect match is found. Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Allele specific amplification technology that depends on selective PCR amplification may be used in conjunction with the instant invention. Oligonucleotides used as primers for specific amplification may carry the mutation or polymorphic region of interest in the center of the molecule. Amplification may then depend on differential hybridization, as described in Gibbs et al. (1989) Nucleic Acids Res. 17:2437-2448), which is herein incorporated by reference, or at the extreme 3' end of one primer where, under appropriate conditions, mismatch can prevent, or reduce polymerase extension.

Direct DNA sequencing, either manual sequencing or automated fluorescent sequencing may detect sequence variation. Another approach is the single-stranded conformation polymorphism assay (SSCP), as described in Orita M, et al. (1989) Proc. Natl. Acad. Sci. USA 86:2766-2770, which is incorporated herein by reference. The fragments that have shifted mobility on SSCP gels may be sequenced to determine the exact nature of the DNA sequence variation. Other approaches based on the detection of mismatches between the two complementary DNA strands include clamped denaturing gel electrophoresis (CDGE), as described in Sheffield V C, et al. (1991) Am. J. Hum. Genet. 49:699-706, which is incorporated herein by reference; heteroduplex analysis (HA), as described in White M B, et al. (1992) Genomics 12:301-306, which is incorporated herein by reference; and chemical mismatch cleavage (CMC) as described in Grompe M, et al., (1989) Proc. Natl. Acad. Sci. USA 86:5855-5892, which is herein incorporated by reference. A review of currently available methods of detecting DNA sequence variation can be found in a review by Grompe (1993), which is incorporated herein by reference. Grompe M (1993) Nature Genetics 5:111-117. Once a mutation is known, an allele specific detection approach such as allele specific oligonucleotide (ASO) hybridization can be utilized to rapidly screen large numbers of other samples for that same mutation. Such a technique can utilize probes that may be labeled with gold nanoparticles to yield a visual color result as described in Elghanian R, et al. (1997) Science 277:1078-1081, which is herein incorporated by reference.

A rapid preliminary analysis to detect polymorphisms in DNA sequences can be performed by looking at a series of Southern blots of DNA cut with one or more restriction enzymes, preferably with a large number of restriction enzymes.

(10) Immuno-PCR and Protein Marker Detection

Immuno-PCR provides an extremely sensitive method to detect proteins. See Sano et al., 1992 Science, 258:120-122. In immuno-PCR, a linker molecule with bi-specific binding affinity for DNA and antibody is used to attach a marker DNA molecule specifically to an antigen-antibody complex, thus resulting in the formation of a specific antigen-antibody-DNA conjugate. The attached marker DNA can be amplified by PCR with the appropriate primers. The presence of specific size PCR products demonstrates that marker DNA molecules are attached specifically to antigen-antibody complexes thereby indicating the presence of antigen. Antigen is immobilized on the surface of microtiter plates and then detected by immuno-PCR. Using this technique, an approximately $10^5$ increase in sensitivity over an alkaline phosphatase conjugated ELISA may be obtained. Sensitivity advantages of immuno-PCR have subsequently been confirmed in assays for mouse anti-lipoprotein IgG (Ruzicka et al., 1993 Science, 260:698-699); a human proto-oncogene protein (Zhou et al., 1993 Nucleic Acid Res., 21:6038-6039); and tumor necrosis factor alpha (Sanna et al., 1995 Proc. Natl. Acad. Sci., 92:272-275).

More recent reports have described advancements in immuno-PCR technology. See, for example, Joerger et al., 1995 Clin. Chem., 41(9):1371-1377. Double-stranded DNA labels may be directly attached to antibodies thus allowing conjugate reagents to be prepared before the assay. A double determinant immuno polymerase chain reaction (double-determinant immuno-PCR) utilizes two monoclonal antibodies, in which the antigens are sandwiched, and a specific DNA molecule is used as a marker. See Suzuki et al., 1995 Jpn. J. Cancer Res., 86:885-889. Instead of the antigen itself, the first monoclonal antibody to bind the circulating antibody is immobilized, the biotinylated second monoclonal antibody is bound to the antigen and free streptavidin is used to attach a biotinylated DNA to the second monoclonal antibody. The biotinylated DNA complexed with antigen-antibody-streptavidin is amplified by PCR, and the products analyzed by Southern blot analysis.

f. Amplification of Genetic Marker

Any method of detection may incorporate a step of amplifying the BD-marker. A BD-marker may be amplified and then detected. Nucleic acid amplification techniques may include cloning, polymerase chain reaction (PCR), reverse transcription PCR (rtPCR), real-time rtPCR, PCR of specific alleles (ASA), ligase chain reaction (LCR), nested polymerase chain reaction, self-sustained sequence replication, transcriptional amplification system, and Q-Beta Replicase, as described in Kwoh, D. Y. et al., 1988, Bio/Technology 6:1197, which is incorporated herein by reference.

Amplification products may be assayed by size analysis, restriction digestion followed by size analysis, detecting specific tagged oligonucleotide oligonucleotide primers in reaction products, allele-specific oligonucleotide (ASO) hybridization, allele specific 5' exonuclease detection, sequencing, and/or hybridization.

PCR-based detection means may include amplification of a plurality of markers simultaneously. PCR primers may be selected to generate PCR products that do not overlap in size and may be analyzed simultaneously. Alternatively, one may amplify different markers with primers that are differentially labeled. Each marker may then be differentially detected. Hybridization-based detection means may allow the differential detection of multiple PCR products in a sample.

Nucleic acid primers and/or oligonucleotides may be used in conjunction with any of the herein described methods and/or kits. The oligonucleotides or primers may be present in the herein described kits and/or used in the herein described methods:

A probe or oligonucleotide may comprise a SNP corresponding to the genetic marker., wherein the fragment comprises the corresponding SNP. The fragment may be between 10 and 500 nucleotides, between 50 and 400 nucleotides, between 100 and 300 nucleotides, between 200 and 250 nucleotides, between 10 and 50 nucleotides, between 10 and 20 nucleotides, between 10 and 30 nucleotides, or between 10 and 40 nucleotides in length.

Any probe, primer, and/or oligonucleotide used as described herein and related to an AKR1B10 sequence, for example, may be purchased from a commercial molecular biology reagent supplier (for example, Applied Biosystems, catalog no. Hs00252524 m1)

3. Method of Treatment

In any patient that carries the BD-marker, an assessment may be made as to whether the subject is an early disease subject, wherein, for example, dysplasia has not occurred, or whether the subject has a dysplasia-associated lesion or mass. The assessment may indicate an appropriate course of preventative or maintenance anti-inflammatory, chemotherapy, and/or antibiotic therapy. These therapies may be administered in different clinical settings during the life of a subject: (1) during early disease a subject may receive anti-inflammatories to delay onset of a bowel disease; (2) after a subject has been diagnosed with having bowel disease, chemotherapy and/or anti-inflammatories and/or antibiotics, for example, may be administered to slow any decline in gastrointestinal function and reduce frequency and morbidity of gastrointestinal exacerbations; and/or (3) during periodic exacerbations in gastrointestinal symptoms, wherein intensive antibiotic and/or chemotherapy and/or anti-inflammatory regimens may be administered to relieve symptomatology and restore gastrointestinal function to baseline values. The BD-marker may be used as a prevention or treatment target by activating or reactivating its gene expression and/or protein function.

a. Predictive Treatment

Provided herein is a method of treating a subject having a BD-marker. Anti-inflammatories may be administered to the subject to prevent or delay onset of bowel disease. Antibiotics may be administered to the subject to prevent or delay onset of bacterial infection. The subject may be undergoing treatment for a gastrointestinal condition.

The treatment of a subject with a particular therapeutic may be monitored by determining protein level, mRNA level, and/or transcriptional level of a gene. The gene may encode an aldo-keto reductase. The gene may be an AKR1B10 gene. Depending on the level detected, the therapeutic regimen may be maintained or adjusted. The effectiveness of treating a subject with an agent may comprise (1) obtaining a preadministration sample from a subject prior to administration of the agent; (2) detecting the level or amount of a protein, RNA or DNA in the preadministration sample; (3) obtaining one or more post-administration samples from the subject; (4) detecting the level of expression or activity of the protein, RNA or DNA in the postadministration sample; (5) comparing the level of expression or activity of the protein, RNA or DNA in the preadministration sample with the corresponding protein, RNA, or DNA in the postadministration sample, respectively; and (6) altering the administration of the agent to the subject accordingly.

Cells of a subject may be obtained before and after administration of a therapeutic to detect the level of expression of genes other than the gene of interest to verify that the therapeutic does not increase or decrease the expression of genes that could be deleterious. Verification may be accomplished by transcriptional profiling. mRNA from cells exposed in vivo to a therapeutic and mRNA from the same type of cells that were not exposed to the therapeutic may be reverse transcribed and hybridized to a chip containing DNA from many genes. The expression of genes in the treated cells may be compared against cells not treated with the therapeutic.

The BD-marker may be used as a marker to identify high-risk subjects such that early intervention may be used to prevent or delay onset of a bowel disease.

b. Maintenance Therapy

Appropriate chemotherapy and/or anti-inflammatory therapy may be essential steps in the management of bowel disease. Selection of a treatment regimen for any given subject in any given setting may be based on periodic identification of surface projections in the gastrointestinal tract. The surface projection may be a dysplasia lesion, an inflamed tissue, or a premalignant adenoma. The presence of a surface lesion, or dysplasia associated lesion, or mass may be indicative of an underlying or associated cancer. Anti-inflammatories and/or antibiotics and/or immune system suppressors may be used for outpatient management of bowel disease and/or for the treatment of bacteria associated with gastrointestinal exacerbations.

c. Antibiotics, Anti-inflammatories, and Immune Suppressors

An antibiotic may be selected from the following: an aminoglycoside, amoxicillin, levofloxacin, dicloxacillin, cephalexin, amoxicillin/clavulanate, erythromycin, clarithromycin, azithromycin, clindamycin, cefuroxime axetil, cefprozil, cefixime, cefpodoxime proxetil, loracarbef, ciprofloxacin, tobramycin, colistin, trimethoprim/sulfamethoxazole, doxycycline, minocycline, cefazolin, nafcillin, vancomycin, β-lactam, ceftazidime, ticarcillin, piperacillin, imipenem, meropenem, aztreonam, an aminoglycoside, amikacin, merpenem, ceftazidime, chloramphenicol, ticarcillin/clavulanate, aztreonam, imipenem, a polypeptide antibiotic, and/or meropenem. The polypeptide antibiotic may be of the polymyxin class of antibiotics. A broad range antibiotic may be used in the regimen. A broad range antibiotic may include levofloxacin or amoxycillin.

An anti-inflammatory agent may be an IL-1 blocker, sulfasalazine, mesalamine, and/or a corticosteroid. An IL-1 blocker may be selected from the following: rilonacept, anakinra, and/or Zn-protoporphyrin (ZnPP).

An immune system suppressor may be any immune suppressing agent. The immune suppressing agent may be azathioprine or mercaptopurine.

An agent may be used to activate, or reactivate the expression and/or function of AKR1B10.

Anti-Diarrheal and Fluid Replacements may be used to relieve diarrhea and crampy abdominal pain, but additional medication may also be necessary. Several antidiarrheal agents may be used, including diphenoxylate, loperamide, and codeine. Subjects who are dehydrated may be treated with fluids and electrolytes The antibiotic, anti-inflammatory, immune system suppressor, anti-diarrheal, or fluid replacement may be formulated for administration by injection, inhalation or insufflation through the nose or mouth, or oral, buccal, parenteral, or rectal administration. The antibiotic or anti-inflammatory may be formulated for parenteral administration by injection, e.g., by bolus injection or continuous infusion. Formulations for injection may be presented in unit dosage form, e.g., in ampules or in multi-dose containers, with an added preservative. The antibiotic or anti-inflammatory may take such a form as a suspension, solution, or emulsion in oily or aqueous vehicles, and may contain formulating agents such as suspending, stabilizing and/or dispersing agents. Antibiotic or anti-inflammatory preparations for oral administration may be suitably formulated to give controlled release of the antibiotic. For buccal administration, the antibiotic may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant. In the case of a pressurized aerosol, the dosage unit may be determined by providing a valve to deliver a metered amount.

An effective dose of the antibiotic may be based upon a culture determination of the bacterial type causing the infection. In addition, an antimicrobial susceptibility report may indicate which families of antibiotic drugs are useful for the particular bacteria recovered from the infection. If the cause of the infection is unclear, but suspected to be due to bacteria, a broad-spectrum antibiotic may be prescribed for controlling a wide variety of bacterial types. In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. Therapeutically effective amounts of an antibiotic may range from approximately 0.05 mg to 10 g per kilogram body weight of the subject per day.

4. Kit

Provided herein is a kit, which may be used for predicting, diagnosing, monitoring, or treating a bowel disease. The kit may comprise a nucleic acid sample or protein sample collecting means. The kit may also comprise a means for determining the presence of a marker, a nucleic acid or protein for use as a positive control, and/or a nucleic acid or protein sampling means. The nucleic acid or protein sampling means may include substrates, such as filter paper, nucleic acid purification reagents, protein purification reagents, such as reaction buffer, polymerase, and dNTPs. Marker detection means may also be included in the kit. Such means may include, specific restriction enzymes, proteases, marker specific oligonucleotides, and degenerate oligonucleotide primers for PCR. The means may comprise any of the oligonucleotides or primers as disclosed herein. The positive control may be used for sequence comparison.

The kit may also comprise one or more containers, such as vials or bottles, with each container containing a separate reagent. The kit may further comprise written instructions, which may describe how to perform or interpret an assay or method described herein.

The present invention has multiple aspects, illustrated by the following non-limiting examples.

EXAMPLES

Example 1

AKR1B10 Expression and Cellular Distribution in Normal Colon

AKR1B10 protein levels and cellular distribution in the colon tissue from one trauma patient, using a specific AKR1B10 antibody, were investigated. Results indicated that AKR1B10 protein in highly expressed in mature epithelial cells. See FIG. 1. Maturation of AKR1B10 expression cells was verified by Ki-67 (a protein marker of proliferating cells) staining in adjacent sections.

With regard to clinical samples, surgically resected specimens (frozen and formalin-fixed, paraffin-embedded) were collected from the NCI-sponsored Co-operative Human Tissue Network (CHTN). This collection included 22 ulcerative colitis, 16 Crohn's disease, 24 adenomas, 78 pairs of gastric adenomcarcinoma (cancer), 27 pairs of small intestine cancer, and 56 pairs of colorectal cancers. Collected tissues were pathologically diagnosed and quality-controlled. Cancer tissues contained more than 80% cancer cells.

Example 2

Frequent Loss of AKR1B10 mRNA and Protein in Frozen Colon Cancer Tissues

Figure 2:
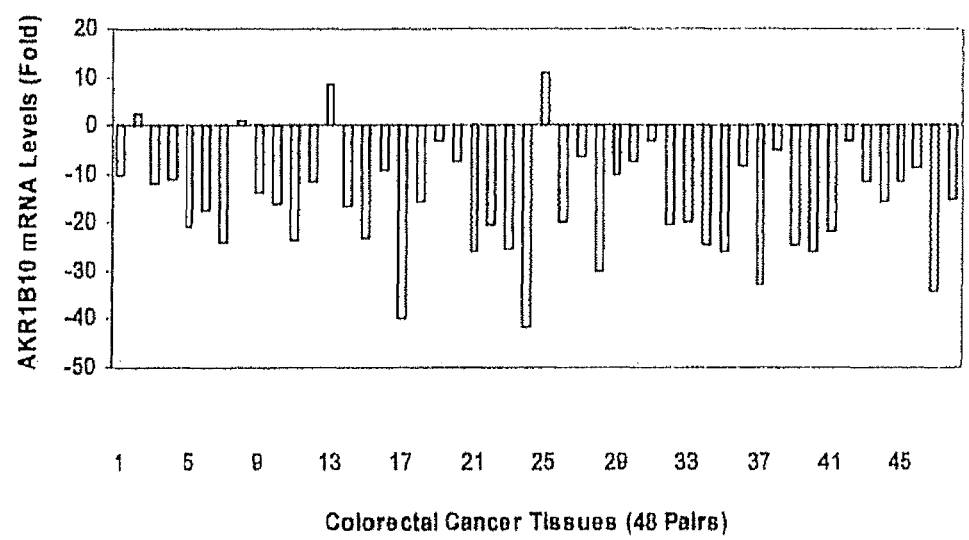
FIG. 2 shows real time RT-PCR for AKR1B10 mRNA levels (A). Western blot for AKR1B10 protein levels in cancer and matching normal tissues is shown in (B).
Figure 2:
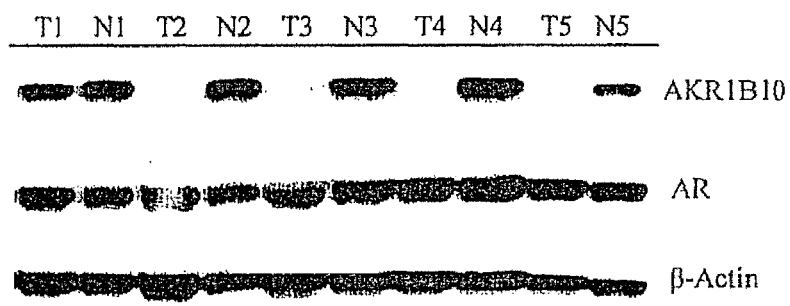

Forty-eight pairs of frozen colorectal cancer and normal surrounding tissues. AKR1B10 mRNA levels were detected by real time RT-PCR with GAPDH as an internal control. The results demonstrated that 44 (91.8%) of 48 paired cancer specimens exhibited a decrease of AKR1B10 mRNA by 3 to 42 fold. See FIG. 2A. AKR1B10 mRNA was slightly higher in the cancer tissues of pairs 2, 8, 13, and 25.

Figure 8:
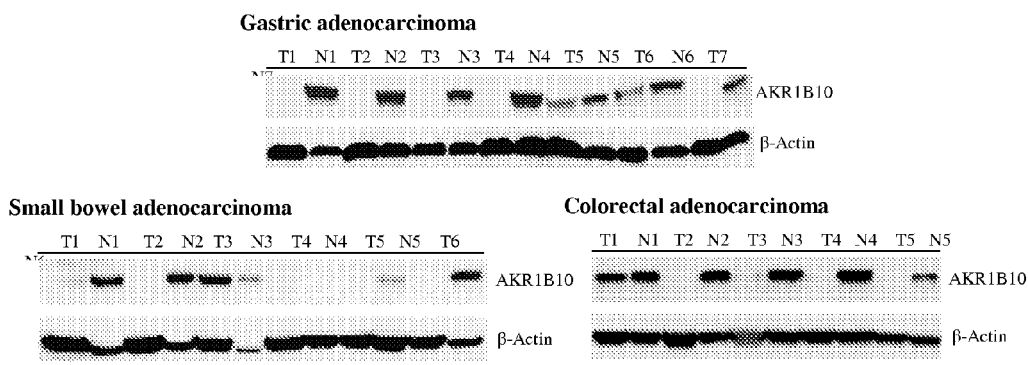
FIG. 8 shows western blot analyses for (A) AKR1B10 protein in gastrointestinal cancer and (B) AKR1B10 protein in gastrointestinal diseases. AKR1B10 protein was undetectable or significantly decreased in gastric, small intestine, and colorectal cancer, inflammatory diseases, and adenomatous polyps.
Figure 8:
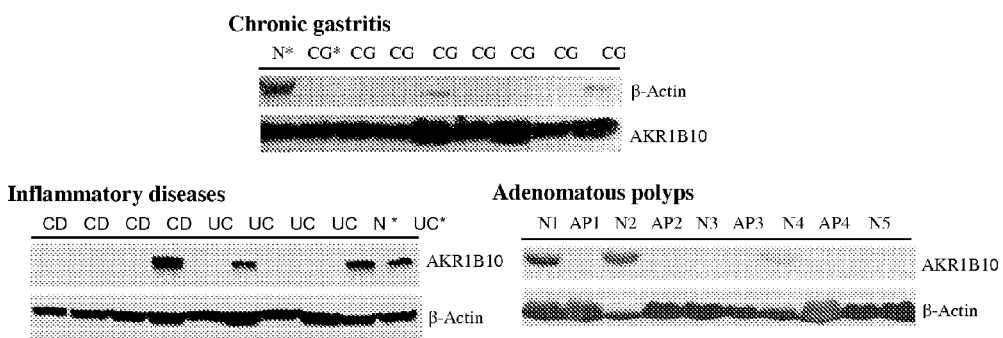
Figure 9:
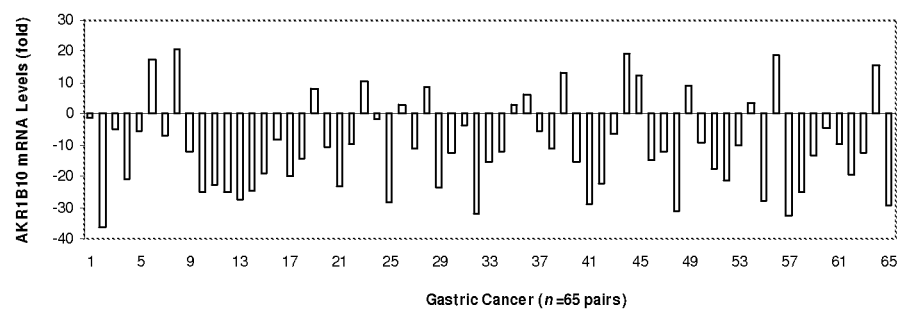
FIG. 9 shows Real-time RT-PCR results relating to decreased levels of AKR1B10 mRNA in gastric, small intestine and colorectal cancer tissues.
Figure 9:
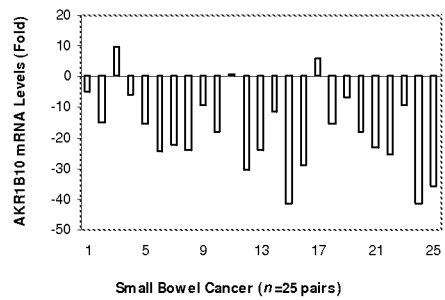
Figure 9:
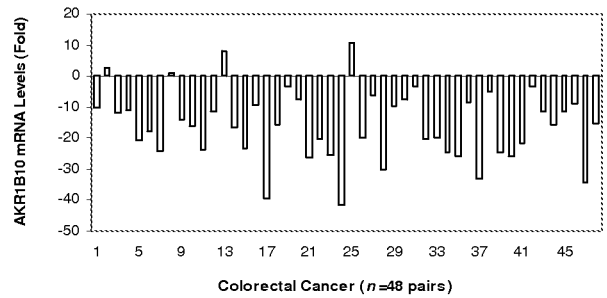

AKR1B10 protein levels in these tissues were examined by Western blot. AKR1B10 protein levels in 5 pairs of colon cancer tissues, in which AKR1B10 was undetectable in tumors 2, 4, and 5, and dramatically decreased in tumor 3. See FIG. 2B. In 78 pairs of gastric adenocarcinomas, AKR1B10 was lost in 44 (56.4%) and significantly decreased in 21 (26.9%) carcinomas, making a total of 83.3% of cancer tissues have not or decreased AKR1B10 expression (FIG. 8). Total RNA was prepared from 65 pairs of gastric tumor tissues and AKR1B10 mRNA levels were determined by real-time reverse transcription polymerase chain reaction (real-time RT-PCR) using TaqMan® Gene Expression Assays (Applied Biosystems, CA). AKR1B10 mRNA was decreased in 50 of 65 (76.9%) paired tumors (FIG. 9).

In 56 pairs of frozen colon adenocarcinomas, AKR1B10 protein was not detected in 40 (71.4%) and significantly reduced in 8 (14.3%) carcinomas, making a total of 85.7% of cancer tissues have not or decreased AKR1B10 expression (FIG. 8). Real-time RT-PCR was performed in 48 pairs of specimens, and results demonstrated that AKR1B10 mRNA was decreased in up to 91.7% tumor tissues (FIG. 9), consistent with Western blot results.

Small intestinal malignancy is less frequent and 27 pairs of frozen adenocarcinoma samples were investigated in this study. Results showed that AKR1B10 was not detected in 19 (70.4%) and significantly decreased in 5 (18.5%) carcinomas, making a total of 85.7% of cancer tissues have not or decreased AKR1B10 expression (FIG. 8). Real-time RT-PCR results demonstrated a decrease of AKR1B10 mRNA in 22 of 25 (88.0%) tumor tissues (FIG. 9).

With regard to real-time polymerase chain reaction, AKR1B10 and GAPDH primer and probe sets were purchased from Applied Biosystems (Foster City, Calif.). Probes were labeled with a report fluorescent dye FAM (6-carbonxyfluorescein) at 5' end and a quencher fluorescent dye TAMRA (6-carbonxytetramethylrhodamine) at 3' end for real-time detection. Total RNA was treated with Rnase-free Dnase 1 and the first-strand cDNA was synthesized from 1 µg of total RNA with oligo dT primer and Superscript II retrotranscriptase, following manufacturer's protocols (Invitrogen, CA). PCR reactions were conducted in a 96-well optical plate using ABI Prism 7500 system. Reaction mixtures (20 µl) contained 5 µl of cDNA templates (5× diluted), 1 µl of primers, and 10 µl of TaqMan universal PCR master mix (Applied Biosystems, CA). PCR cycling conditions were as follows: 95° C. 15 sec and 60° C. 1 minute, after an initial denature at 95° C. for 5 min. Each reaction was duplicated. Variability of Ct values between duplicates with the same run was no more than 3%, while the coefficient of variation (CV) between different runs was no more than 5%. GAPDH mRNA in each sample was run in parallel for an internal control. After correction by GAPDH mRNA, AKR1B10 mRNA levels in tumor tissues were expressed by subtracting the mRNA in matching normal tissues.

Total RNA was extracted using Trizol reagent (Invitrogen, CA). In 1 ml of Trizol reagent 50 mg tissue was homogenized on ice. After incubation for 5 min., 0.2 ml of chloroform was added and mixed vigorously for 15 sec. Supernatants containing RNA were collected at 12,000×g for 15 minutes at 4° C. Total RNA was precipitated with 0.5 ml of 2-propanol at 12,000×g for 10 minutes and then washed with 70% ethanol. RNA quality was checked on formaldehyde denaturing agarose gel and quantity was determined by OD260 using a spectrophotometer (Beckman, Calif.). Bottom phase or RNA extraction was mixed with 1.5 ml isopropanol and incubated at room temperature for 10 minutes. Protein precipitates were collected at 12,000×g at 4° C. for 10 minutes and washed 3 times with 0.3 M guanidine hydrochloride in 95% ethanol. Proteins were vacuum-dried for 5 minutes and then dissolved in 1% SDS at 50° C. overnight.

Example 3

Tissue Microarray (TMA) Analysis of Archived Colorectal Cancer and Retrospective Study of AKR1B10 Expression To define the effects of AKR1B10 loss on tumor progression and patient survival, a pool of 629 colorectal tissues with pathological and follow-up data were analyzed by a tissue microarray assay (TMA assay). After evaluation by two independent investigators, a total of 592 tissues from different patients showed a quality staining and were scored for AKR1B10 expression. Of the 592 tissues, AKR1B10 staining was not visible (−) in 374 (63.13%) and weakly positive (+) in 146 (24.66%), as a total of 520 (87.84%) colorectal cancer tissues with AKR1B10 loss or reduction. The other 72 (12.16%) samples were stained positively (++). See FIG. 3. One spot showed a conjunction area of tumor and adjacent hyperplasia. In this region, AKR1B10 was strongly stained in hyperplastic but not malignant cells, indicating the tumor-specificity of AKR1B10 loss. See FIG. 4, wherein Area 1 indicates cancer cells with no AKR1B10 staining and Area 2 denotes a hyperplastic villus with AKR1B10 expression.

Figure 5:
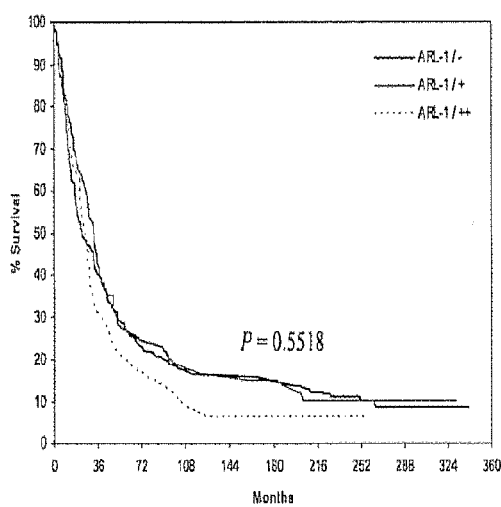
FIG. 5 shows a Kaplan-Meier analysis of disease-associated survival.
Figure 5:
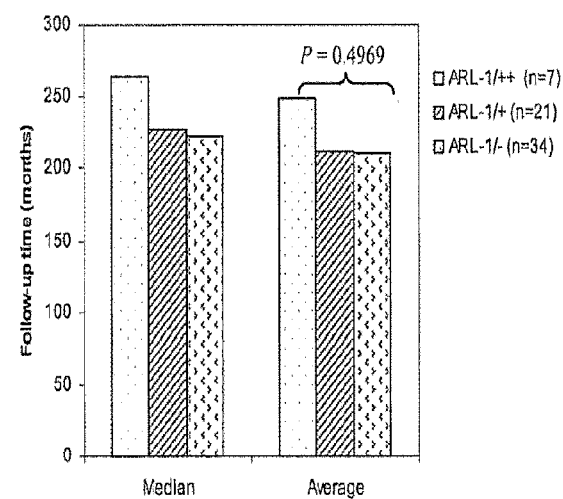

A retrospective study of this 592 colorectal cancer data pool demonstrated that loss or reduction of AKR1B10 protein in colorectal cancer did not correlate with patient age and sex, or with tumor T-pathology, N-pathology, histological stage, and cell differentiation. See Table 2. AKR1B10 loss had no effect on disease-associated patient survival. See FIG. 5A. Follow-up time of disease-free alive patients was slightly longer in AKR1B10 positive patients than in weakly positive and negative patients, but there is no statistical significance (p=0.4969). See FIG. 5B. These data indicate that AKR1B10 loss may not be a prognostic marker.

Immunohistochemistry study of paraffin sections or tissue microarrays was initiated by deparaffinizing and rehydrating as follows: two times for 10 min in xylene, once for 2 min in 100% ethanol, once for 2 min in 90% ethanol, and once for 2 min in 70% ethanol. In a Coplin jar with antigen retrieval solution (10 mM citric acid, pH 6.0), sections were completely immersed and microwaved (at 700 watts) for 5-20 min. After cooling for 20 min at room temperature (RT), sections were rinsed in deionized water two times for 5 min each. Endogenous peroxidase was inactivated with 0.3% H2O2 at room temperature for 20 min. Incubation with anti-AKR1B10 (1:5) or acrolein (1:10, Advanced Targeting System, CA) was performed at 4° C. overnight. After being washed by PBS, the sections were incubated with horseradish peroxidase conjugated secondary antibody (1:100) at 37° C. for 10-30 min. Thereafter, sections were counter-stained with hematoxylin to indicate nuclei and mounted with cover sides. For immunocytochemistry, cells cultured on cover slides were fixed in ice-cold methanol for 10 min and ice-cold acetone for additional 1 min. After being exposed to 0.3% H2O2 at RT for 20 min, cells were incubated with acrolein antibody (1:10) at 4° C. overnight, followed by incubation with secondary antibody and DAB exposure.

Figure 3:
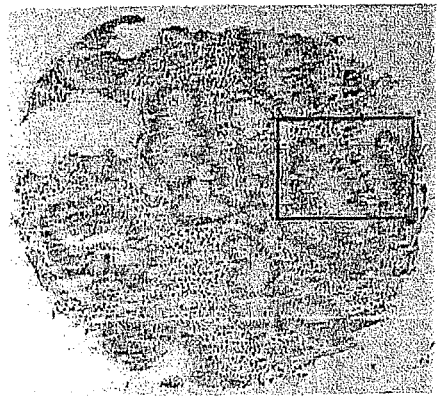
FIG. 3 shows scoring for AKR1B10 expression in paraffin-embedded colorectal cancer tissues.
Figure 3:
Figure 3:
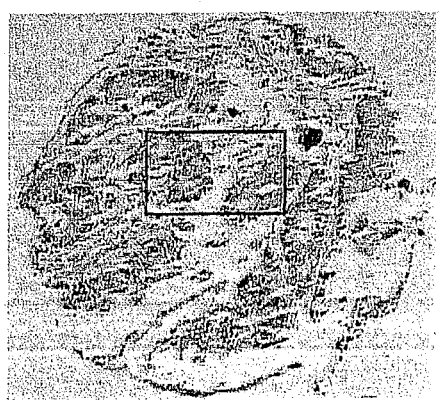
Figure 3:
Figure 3:
Figure 3:
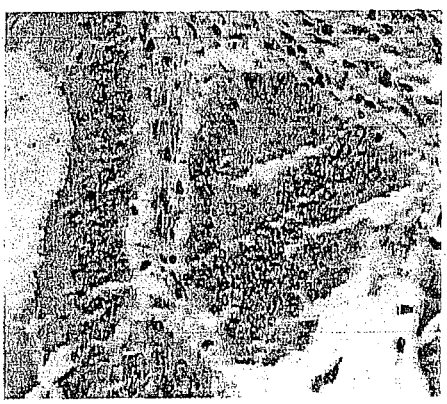
Figure 4:
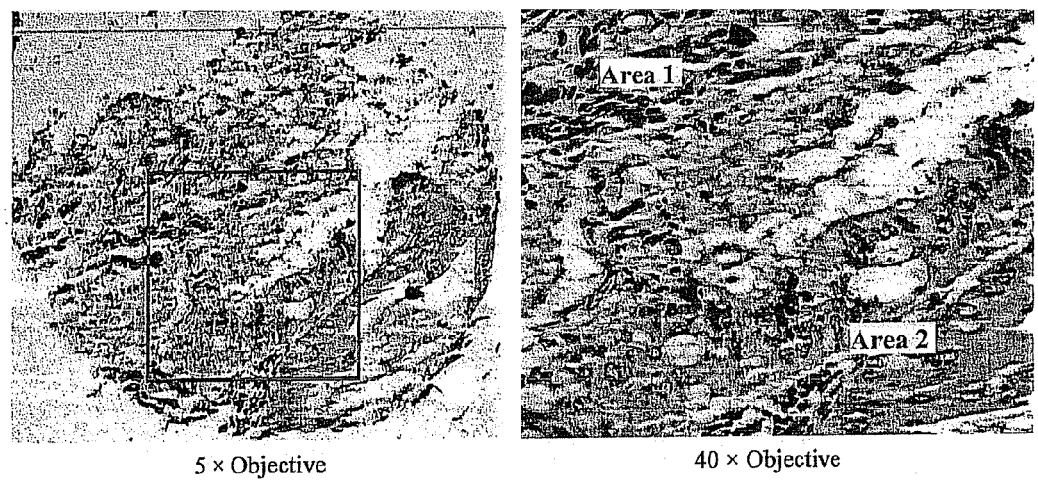
FIG. 4 shows a punch of tissue microarray stained with AKR1B10 specific antibody, specifically demonstrating the loss of AKR1B10 protein in the tumor cells, but not in the adjacent non-tumor cells.

Colorectal cancer TMA was obtained from Tissue Microarray Facility, Department of Pathology at Yale University. Formalin-fixed and paraffin-embedded tissues were used, which represents a collection started from the 1960s. All tissues have complete pathological reports and follow-up data. This TMA contained 649 spots, which consisted of 629 colorectal cancers, 10 normal colons, and 10 cultured cells. Immunohistochemical staining of the TMA was performed using the conditions characterized for paraffin sections described above. AKR1B10 staining was evaluated independently by a researcher and a pathologist and classified as follows: negative (no staining), weakly positive (+, low-intensity staining), and positive (++, high intensity staining). A set of negative, weakly positive and positive staining tissues are shown in FIG. 3.

One way analysis of variance (ANOVA) was used to compare the three AKR1B10 groups on age at diagnosis. Kruskal-Wallis tests were used to compare the groups on T-pathology, N-pathology and histological stage. Chi-square tests of independence, or exact tests as appropriate, were used to compare the groups on the proportion of subjects with different histological grades and types and on their survival status. Kaplan-Meier survival curves were computed to estimate the survival rates at 1, 3, 5, and 8 years. Curves were compared using the log-rank test. Results were considered statistically significant for $p<0.05$.

TABLE 2

AKR1B10 Levels in Tumors (n = 592)

|  | Positive | Weakly Positive | Negative | p-Value[2] |
|---|---|---|---|---|
| Subtotal | 72 (12.16%) | 146 (24.66%) | 374 (63.18%) |  |
| Age |  |  |  | 0.0952 |
| Mean | 70.15 | 67.43 | 67.09 |  |
| Median | 71 | 68 | 68 |  |
| Sex |  |  |  | 0.5517 |
| Male | 38 | 66 | 183 |  |
| Female | 34 | 80 | 191 |  |
| Tumor types |  |  |  | 0.2732 |
| Adenocarcinoma | 65 | 136 | 334 |  |
| M. adenocarcinoma | 3 | 5 | 20 |  |
| Others | 1 | 2 | 17 |  |
| T-pathology |  |  |  | 0.4960 |
| T0 | 1 | 0 | 2 |  |
| T1 | 0 | 7 | 13 |  |
| T2 | 25 | 37 | 121 |  |
| T3 | 38 | 84 | 196 |  |
| T4 | 0 | 1 | 2 |  |
| N-pathology |  |  |  | 0.9604 |
| N0 | 35 | 79 | 176 |  |
| N1 | 18 | 39 | 93 |  |
| N2 | 11 | 19 | 47 |  |
| Differentiation |  |  |  | 0.2512 |
| Well | 31 | 47 | 110 |  |
| Moderate | 25 | 57 | 144 |  |
| Poor | 4 | 15 | 42 |  |
| Stages |  |  |  | 0.8679 |
| 1 | 15 | 26 | 83 |  |
| 2 | 19 | 39 | 88 |  |
| 3 | 27 | 58 | 141 |  |
| 4 | 7 | 15 | 42 |  |
| Metastasis |  |  |  | 0.7269 |
| Localized | 33 | 57 | 164 |  |
| Regional | 29 | 69 | 151 |  |
| Distant | 10 | 19 | 53 |  |
| Survival |  |  |  | 0.3621 |
| Alive w disease | 2 | 9 | 22 |  |
| Alive w/o disease | 7 | 21 | 34 |  |
|  | 30 | 68 | 176 |  |
| Dead w disease | 33 | 48 | 142 |  |
| Dead w/o disease |  |  |  |  |

Example 4

AKR1B10 Expression in Chronic Gastritis, Crohn's Disease, and Ulcerative Colitis Chronic atrophic gastritis, ulcerative colitis, and Crohn's disease are chronic inflammatory diseases associated with an increased risk of developing cancer. In this study, we examined AKR1B10 expression in chronic gastritis (tissue microarray), Crohn's disease (frozen surgical specimens), and ulcerative colitis (frozen surgical specimens). As summarized in Table 3, AKR1B10 was undetectable in 35 (68.6%) of 51 chronic atrophic gastritis with intestinal metaplasia, 2 (40.0%) of 5 chronic superficial gastritis, 16 (80.0%) of 20 Crohn's disease, and 17 (77.3%) of 22 ulcerative colitis (FIG. 8). Real-time RT-PCR was not conducted in the frozen tissues due to the lack of the normal adjacent tissues. AKR1B10 expression in adenomatous polyps, a precursor disease of GI adenocarcinomas was also examined; and results showed that this protein was lost in 7 (70.0%) of 10 gastric and 19 (79.2%) of 24 colon polyps (FIG. 8).

TABLE 3

|  | AKR1B10 | |
|---|---|---|
|  | Negative | Positive |
| Gastric diseases |  |  |
| Chronic atrophic gastritis with intestinal metaplasia (n = 51)[1] | 35 (68.6%) | 16 (31.4%) |
| Chronic superficial gastritis (n = 5)[1] | 2 (40.0%) | 3 (60.0%) |
| Hyperplastic polyps (n = 10)[2] | 7 (70.0%) | 3 (30.0%) |
| Intestinal diseases |  |  |
| Ulcerative colitis (n = 22)[2] | 17 (77.3%) | 5 (22.7%) |
| Crown's disease (n = 20)[2] | 16 (80.0%) | 4 (20.0%) |
| Polyps/adenomas (n = 24)[2] | 19 (79.2%) | 5 (20.8%) |

[1]Tissue microarray detected by immunohistochemistry.
[2]Frozen tissues detected by Western blot Example 5

AKR1B10 Protein Loss and Acrolein-Induced Protein Damage in IBD Tissues

Figure 6:
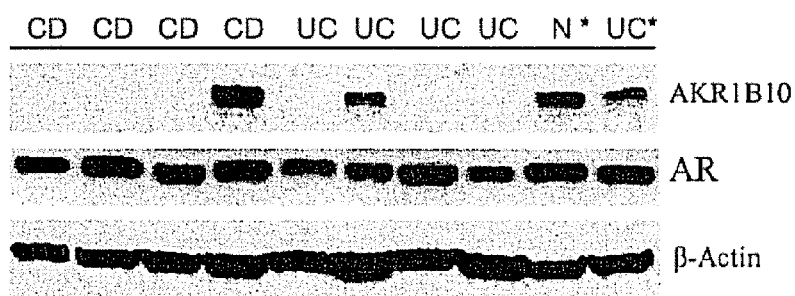
FIG. 6 shows a western blot for AKR1B10 protein levels in inflammatory tissues (A). A western blot for acrolein-protein adduct levels in inflammatory tissues is shown in (B). For both (A) and (B), CD, Crohn's disease; UC, ulcerative colitis; and N, normal.
Figure 6:
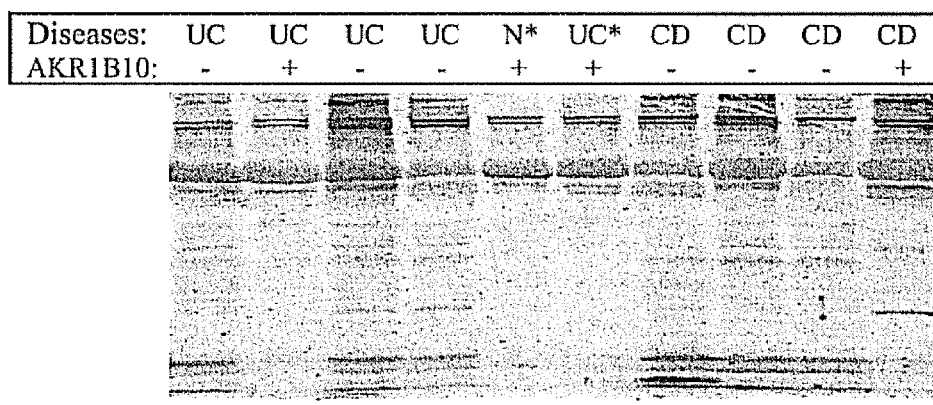

AKR1B10 protects cells from acrolein lesions, a pathogenic factor of colorectal cancer. Therefore, acrolein lesions of the inflammatory tissues were evaluated by examining acrolein-protein adducts. As shown in FIG. 6B, levels of acrolein-protein adducts were notably higher in the inflammatory tissues without AKR1B10 expression. AR protein levels were not changed in these specimens. There is a reciprocal correlation between AKR1B10 and acrolein protein levels in intestinal inflammatory tissues.

Western blots were performed as proteins (approx. 50 μg) were separated on 12% SDS-PAGE and blotted onto a pure nitrocellulose membrane (Bio-Rad, CA) at 180 mA for 2 hours. After being blocked with 5% skim mild in PBS at room temperature for 45 minutes, membranes were incubated with AKR1B10 (1:500), aldose reductase (1:500), or acrolein (1:500, Advanced Targeting System, CA) antibodies in the same buffer at 4° C. overnight, followed by incubation with goat anti-rabbit or mouse IgG (1:2000) for 1 hour. Antibody binding was detected using enhanced chemiluminescence system (Pierce, 11). Loading amounts of proteins were corrected by re-probing membranes with β-actin monoclonal antibody (1:40,000, Sigma, Mo.).

Example 6

Acrolein Damage of HCT-8 Cells Induced by AKR1B10 Silencing

Figure 7:
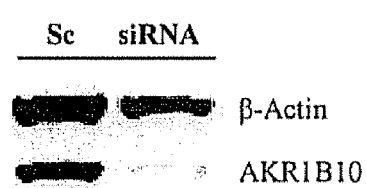
FIG. 7 shows a western blot and immunocytochemistry analysis of AKR1B10-downregulated HCT-8 cells (a human colon adenocarcinoma cell line). Cells were analyzed for acrolein damage. In (A), a western blot that shows AKR1B10 knockdown. In (B), a western blot that shows acrolein-protein adducts. In (C), immunocytochemistry showing staining intensity of acrolein-protein adducts.
Figure 7:
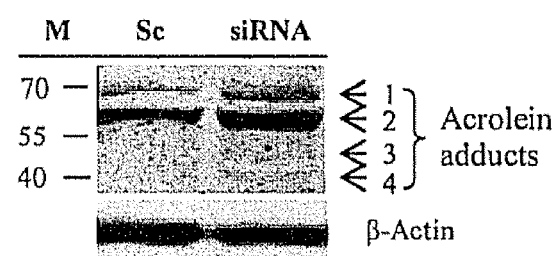
Figure 7:
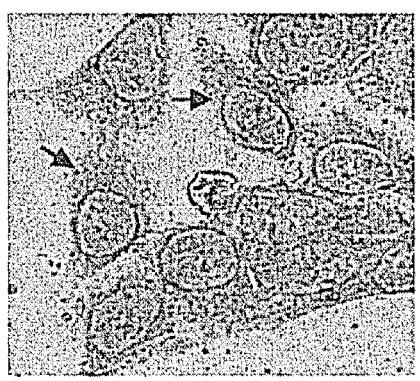
Figure 7:
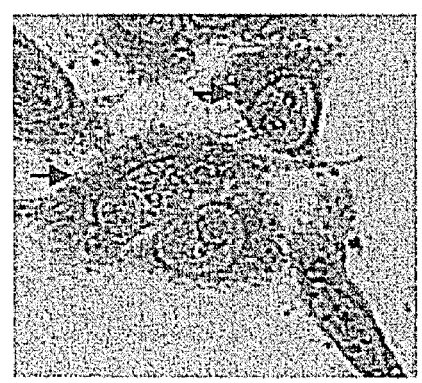

AKR1B10 protein was downregulated up to approximately 95% by synthesized siRNA. See FIG. 7A. As a result, acrolein-protein adducts in these cells were notably increased as demonstrate by Western blot and immunocytochemistry. See FIGS. 7B and 7C. In AKR1B10 knockdown cells, bands 1 and 2 are much stronger than in the scrambled control, and two additional weak bands (bands 3 and 4) appeared. Immunocytochemistry demonstrated that AKR1B10 silencing cells stained darker with rougher brown granules, compared to the scrambled control. These data indicate that AKR1B10 gene silencing resulted in increased endogenous acrolein damage in HCT-8 cells.

With respect to cell culture and AKR1B10 silencing by siRNA, HCT-8 cells, purchased from American Type Culture Collection (Manassas, Va.), were maintained in RPMI-1640 medium (Hyclone, Utah) containing 10% fetal bovine serum (FBS), 2 mM glutamine, 100 U/ml penicillin, and 100 μg/ml streptomycin at 37° C., 5% $CO_2$. AKR1B10 gene silencing was conducted using siRNAs targeted to (1) an encoding region of AKR1B10 (SEQ ID NO:3), and (2) a 3' untranslational region of AKR1B10 (SEQ ID NO:4). See Table 4. Briefly, HCT-8 cells (3.5×104 in OptiMEM 1 medium) were mixed gently with small-interfering RNA (siRNA) and OligofectAMINE (Invitrogen, CA) in a volume of 0.5 ml, following manufacturer's instructions, and then incubated at 37° C., 5% $CO_2$ for 4 hours, followed by the addition of an equal volume of fresh medium containing 20% FBS. Cells were continuously cultured until harvest.

TABLE 4

| siRNA Sequence | SEQ ID NO. |
|---|---|
| 5'GCAAGUUGUGGCCCACUUUtt | SEQ ID NO: 3 |
| 5'CGAGAAUCGAGGUGCUGUUtt | SEQ ID NO: 4 |

Total RNA was extracted using Trizol reagent (Invitrogen, CA). In 1 ml of Trizol reagent 50 mg tissue was homogenized on ice. After incubation for 5 min., 0.2 ml of chloroform was added and mixed vigorously for 15 sec. Supernatants containing RNA were collected at 12,000×g for 15 minutes at 4° C. Total RNA was precipitated with 0.5 ml of 2-propanol at 12,000×g for 10 minutes and then washed with 70% ethanol. RNA quality was checked on formaldehyde denaturing agarose gel and quantity was determined by OD260 using a spectrophotometer (Beckman, Calif.). Bottom phase or RNA extraction was mixed with 1.5 ml isopropanol and incubated at room temperature for 10 minutes. Protein precipitates were collected at 12,000×g at 4° C. for 10 minutes and washed 3 times with 0.3 M guanidine hydrochloride in 95% ethanol. Proteins were vacuum-dried for 5 minutes and then dissolved in 1% SDS at 50° C. overnight.

I claim:

1. A method for detecting, and/or monitoring, a non-cancerous colorectal disease in a subject, comprising:
   (a) providing a sample from a subject;
   (b) measuring an amount of a BD-marker protein in the subject sample using an immunoassay;
   (c) measuring an amount of BD-marker protein in a control sample using the immunoassay;
   (d) comparing the amount from (b) to the amount from (c) to detect a difference between the amount of the BD-marker protein in the control sample and the amount of the BD-marker protein in the subject sample; and
   (e) diagnosing the subject as having a non-cancerous colorectal disease when the difference detected in step (d) shows a loss of the BD-marker protein or a reduction in the amount of the BD-marker protein in the subject sample relative to the amount of the BD-marker protein in the control sample, wherein the BD-marker protein is AKR1B10, and further wherein the non-cancerous colorectal disease is selected from the group consisting of non-cancerous rectal disease, non-cancerous chronic colorectal disease, non-cancerous chronic inflammatory bowel disease, adenoma, inflammatory bowel disease, ulcerative colitis, and Crohn's disease.

2. The method of claim 1, wherein the control sample is from a subject that does not have a colorectal disease.

3. The method of claim 1, wherein the control sample is taken from the subject being monitored.

4. The method of claim 3, wherein the control sample is taken before the subject sample is taken.

5. The method of claim 1, wherein the sample comprises protein.

6. The method of claim 1, wherein the amount of AKR1B10 in the subject sample is lower than the amount of AKR1B10 in the control sample.

7. The method of claim 6, wherein the amount of AKR1B10 in the subject sample is between 1 and 40-fold lower than the amount of AKR1B10 in the control sample.

8. The method of claim 1, wherein the sample comprises a stool sample.

9. The method of claim 8, wherein the amount of AKR1B10 marker protein is determined by the immunoassay in which the sample is contacted by an antibody which specifically binds to AKR1B10.

10. The method of claim 9, wherein the immunoassay is an ELISA.

11. The method of claim 1, wherein the sample from the subject comprises a tissue sample.

12. The method of claim 11, wherein the amount of AKR1B10 marker protein is determined by an assay selected from the group consisting of: Western blot and immunohistochemistry.

13. A method for detecting or monitoring a non-cancerous colorectal disease in a subject, comprising:
   (a) providing a sample from a subject;
   (b) measuring an amount of AKR1B10 marker protein in the subject sample; and
   (c) diagnosing the subject as having the non-cancerous colorectal disease when the amount of AKR1B10 marker protein is not detectable in the subject sample, wherein the non-cancerous colorectal disease is at least one of rectal disease, chronic colorectal disease, chronic inflammatory bowel disease, adenoma, inflammatory bowel disease, ulcerative colitis, and Crohn's disease.

14. The method of claim 13, wherein the sample from the subject comprises a stool sample.

15. The method of claim 14, wherein the amount of AKR1B10 marker protein is determined by the immunoassay in which the sample is contacted by an antibody which specifically binds to AKR1B10.

16. The method of claim 15, wherein the immunoassay is an ELISA.

17. The method of claim 13, wherein the sample from the subject comprises a tissue sample.

18. The method of claim 17, wherein the amount of AKR1B10 marker protein is determined by an assay selected from the group consisting of: Western blot and immunohistochemistry.

* * * * *

```
SEQUENCE LISTING

<160> NUMBER OF SEQ ID NOS: 4

<210> SEQ ID NO 1
<211> LENGTH: 1337
<212> TYPE: DNA
<213> ORGANISM: Homo sapiens

<400> SEQUENCE: 1
caaaaacagc aacagaaagc aggacgtgag acttctacct gctcactcag aatcatttct      60
gcaccaacca tggccacgtt tgtggagctc agtaccaaag ccaagatgcc cattgtgggc     120
ctgggcactt ggaagtctcc tctcggcaaa gtgaagaag cagtgaaggt ggccattgat     180
gcaggatatc ggcacattga ctgtgcctat gtctatcaga atgaacatga agtgggggaa     240
gccatccaag agaagatcca agagaaggct gtgaagcggg aggacctgtt catcgtcagc     300
aagttgtggc ccactttctt tgagagaccc cttgtgagga aagcctttga gaagaccctc     360
aaggacctga agctgagcta tctggacgtc tatcttattc actggccaca gggattcaag     420
tctggggatg accttttccc caaagatgat aaaggtaatg ccatcggtgg aaaagcaacg     480
ttcttggatg cctgggaggc catggaggag ctggtggatg aggggctggt gaaagccctt     540
ggggtctcca atttcagcca cttccagatc gagaagctct tgaacaaacc tggactgaaa     600
tataaaccag tgactaacca ggttgagtgt cacccatacc tcacgcagga gaaactgatc     660
cagtactgcc actccaaggg catcaccgtt acggcctaca gcccctggg ctctccggat     720 agaccttggg ccaagccaga agacccttcc ctgctggagg atccccaagat taaggagatt     780 gctgcaaagc acaaaaaaac cgcagcccag gttctgatcc gtttccatat ccagaggaat     840
gtgattgtca tccccaagtc tgtgacacca gcacgcattg ttgagaacat tcaggtctttt     900 gactttaaat tgagtgatga ggagatggca accatactca gcttcaacag aaactggagg     960
```

-continued

```
gcctgtaacg tgttgcaatc ctctcatttg gaagactatc ccttcgatgc agaatattga    1020
ggttgaatct cctggtgaga ttatacagga gattctcttt cttcgctgaa gtgtgactac    1080
ctccactcat gtcccatttt agccaagctt atttaagatc acagtgaact tagtcctgtt    1140
atagacgaga atcgaggtgc tgttttagac atttatttct gtatgttcaa ctaggatcag    1200
aatatcacag aaaagcatgg cttgaataag gaaatgacaa ttttttccac ttatctgatc    1260
agaacaaatg tttattaagc atcagaaact ctgccaacac tgaggatgta aagatcaata    1320
aaaaaaataa taatcat                                                    1337

<210> SEQ ID NO 2
<211> LENGTH: 316
<212> TYPE: PRT
<213> ORGANISM: Homo sapiens

<400> SEQUENCE: 2

Met Ala Thr Phe Val Glu Leu Ser Thr Lys Ala Lys Met Pro Ile Val
  1               5                  10                  15

Gly Leu Gly Thr Trp Lys Ser Pro Leu Gly Lys Val Lys Glu Ala Val
                 20                  25                  30

Lys Val Ala Ile Asp Ala Gly Tyr Arg His Ile Asp Cys Ala Tyr Val
             35                  40                  45

Tyr Gln Asn Glu His Glu Val Gly Glu Ala Ile Gln Glu Lys Ile Gln
         50                  55                  60

Glu Lys Ala Val Lys Arg Glu Asp Leu Phe Ile Val Ser Lys Leu Trp
 65                  70                  75                  80

Pro Thr Phe Phe Glu Arg Pro Leu Val Arg Lys Ala Phe Glu Lys Thr
                 85                  90                  95

Leu Lys Asp Leu Lys Leu Ser Tyr Leu Asp Val Tyr Leu Ile His Trp
                100                 105                 110

Pro Gln Gly Phe Lys Ser Gly Asp Asp Leu Phe Pro Lys Asp Asp Lys
            115                 120                 125

Gly Asn Ala Ile Gly Gly Lys Ala Thr Phe Leu Asp Ala Trp Glu Ala
        130                 135                 140

Met Glu Glu Leu Val Asp Glu Gly Leu Val Lys Ala Leu Gly Val Ser
145                 150                 155                 160

Asn Phe Ser His Phe Gln Ile Glu Lys Leu Leu Asn Lys Pro Gly Leu
                165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
        195                 200                 205

Ala Tyr Ser Pro Leu Gly Ser Pro Asp Arg Pro Trp Ala Lys Pro Glu
    210                 215                 220

Asp Pro Ser Leu Leu Glu Asp Pro Lys Ile Lys Glu Ile Ala Ala Lys
225                 230                 235                 240

His Lys Lys Thr Ala Ala Gln Val Leu Ile Arg Phe His Ile Gln Arg
                245                 250                 255

Asn Val Ile Val Ile Pro Lys Ser Val Thr Pro Ala Arg Ile Val Glu
            260                 265                 270

Asn Ile Gln Val Phe Asp Phe Lys Leu Ser Asp Glu Glu Met Ala Thr
        275                 280                 285

Ile Leu Ser Phe Asn Arg Asn Trp Arg Ala Cys Asn Val Leu Gln Ser
    290                 295                 300
```

-continued

```
Ser His Leu Glu Asp Tyr Pro Phe Asp Ala Glu Tyr
305                 310                 315

<210> SEQ ID NO 3
<211> LENGTH: 21
<212> TYPE: DNA
<213> ORGANISM: Artificial
<220> FEATURE:
<223> OTHER INFORMATION: siRNA targeted to AKR1B10.

<400> SEQUENCE: 3
gcaaguugug gcccacuuut t                                             21

<210> SEQ ID NO 4
<211> LENGTH: 21
<212> TYPE: DNA
<213> ORGANISM: Artificial
<220> FEATURE:
<223> OTHER INFORMATION: siRNA targeted to AKR1B10.

<400> SEQUENCE: 4
cgagaaucga ggugcuguut t                                             21
```